(12) United States Patent
Bertoli

(10) Patent No.: US 11,633,177 B2
(45) Date of Patent: Apr. 25, 2023

(54) RETRACTOR DEVICE FOR BREAST RECONSTRUCTION SURGERY

(71) Applicant: DECO MED SRL, Marcon (IT)

(72) Inventor: Giovanni Bertoli, Marcon (IT)

(73) Assignee: DECO MED SRL, Marcon (IT)

( * ) Notice: Subject to any disclaimer, the term of this patent is extended or adjusted under 35 U.S.C. 154(b) by 0 days.

(21) Appl. No.: 17/414,847

(22) PCT Filed: Dec. 12, 2019

(86) PCT No.: PCT/IT2019/050264
§ 371 (c)(1),
(2) Date: Jun. 16, 2021

(87) PCT Pub. No.: WO2020/129101
PCT Pub. Date: Jun. 25, 2020

(65) Prior Publication Data
US 2022/0071614 A1  Mar. 10, 2022
US 2022/0225976 A2  Jul. 21, 2022

(30) Foreign Application Priority Data
Dec. 17, 2018  (IT) ................ 102018000011130

(51) Int. Cl.
*A61B 17/02*  (2006.01)
*A61B 17/00*  (2006.01)

(52) U.S. Cl.
CPC .... *A61B 17/02* (2013.01); *A61B 2017/00796* (2013.01)

(58) Field of Classification Search
CPC .......... A61B 17/02; A61B 2017/00796; A61B 2017/008
See application file for complete search history.

(56) References Cited

U.S. PATENT DOCUMENTS

| | | | | |
|---|---|---|---|---|
| 730,284 A | * | 6/1903 | Monosmith | A61B 17/0206 600/219 |
| 5,351,680 A | * | 10/1994 | Jung | A61B 17/02 600/214 |
| 5,380,331 A | * | 1/1995 | Mikhail | A61B 17/02 606/53 |
| 8,784,101 B1 | * | 7/2014 | Engeron | A61B 17/02 433/140 |

(Continued)

FOREIGN PATENT DOCUMENTS

WO    2007002405 A2    1/2007

OTHER PUBLICATIONS

Search Report dated Apr. 8, 2020 in corresponding International Application No. PCT/IT2019/050264, 4 pages.

(Continued)

*Primary Examiner* — Ellen C Hammond
(74) *Attorney, Agent, or Firm* — MH2 Technology Law Group LLP

(57) ABSTRACT

A retractor device for breast reconstruction surgery which entails the effective exposure and visibility of the breast pocket and, at the same time, does not compromise the integrity of the subcutaneous flap, resulting in a positive outcome of the breast reconstruction procedure generally, but not exclusively, performed using a prepectoral (or subcutaneous) acellular biological matrix.

6 Claims, 6 Drawing Sheets

(56) References Cited

U.S. PATENT DOCUMENTS

Figure 1:
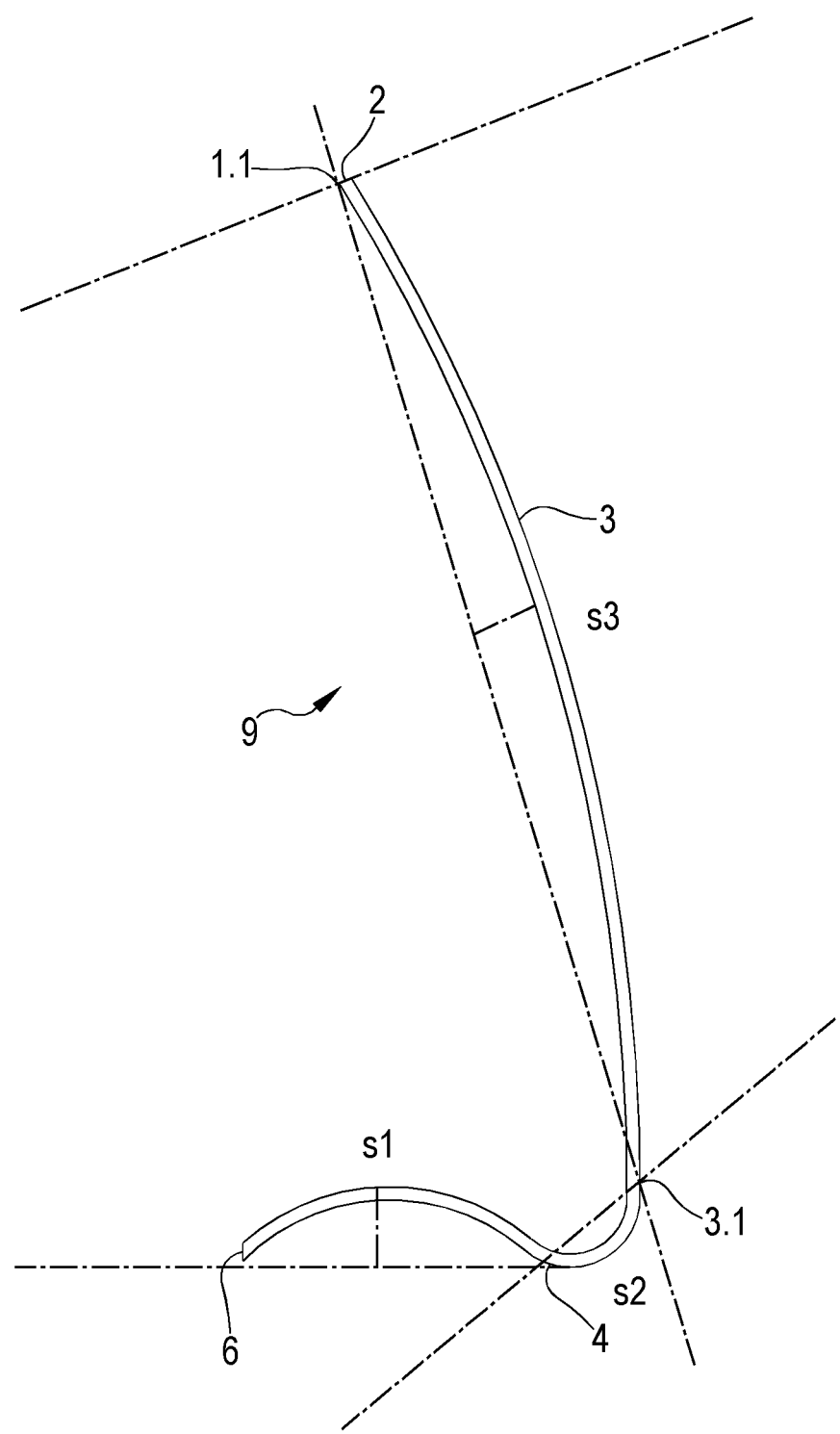

2010/0125171 A1\* 5/2010 Kelner ................ A61B 17/02
  600/201
2011/0172496 A1\* 7/2011 Capizzi ................ A61B 17/02
  600/235

OTHER PUBLICATIONS

Written Opinion dated Apr. 8, 2020 in corresponding International Application No. PCT/IT2019/050264, 8 pages.

\* cited by examiner

RETRACTOR DEVICE FOR BREAST RECONSTRUCTION SURGERY

CROSS-REFERENCE TO RELATED APPLICATIONS

This application is a U.S. National Stage application of PCT/IT2019/050264 filed Dec. 12, 2019, pending, which claims priority to Italian Patent Application No. 102018000011130 filed Dec. 17, 2018, the entire disclosures of which are hereby incorporated by reference in their entireties.

This application concerns a retractor device for breast reconstruction surgery.

Specifically, the present patent application relates to a retractor type medical device which entails the effective exposure and visibility of the breast pocket and, at the same time, does not compromise the integrity of the subcutaneous flap, resulting in a positive outcome of the breast reconstruction procedure generally, but not exclusively, performed using a prepectoral (or sub-cutaneous) acellular biological matrix.

As is known, breast reconstruction with the use of prostheses has undergone an evolution as a result of the introduction of a new prepectoral method.

Prior art, as described in patent application EP2903563, requires a change of the plane on which the prosthetic itself is to be positioned. Placement is subglandular rather than submuscular.

The silicone prosthesis is wrapped with an acellular biological matrix, which in turn interfaces with the subcutaneous flap, makes it possible to avoid complications, such as capsular contracture, described previously by various authors.

The change of anatomical plane, which becomes more superficial, also requires changes to the techniques involved in the surgical procedure. They must preserve the integrity of the tissues that make up the suprapectoral plane and, more specifically, the subcutaneous flap. The base of the new plane is the pectoralis major muscle covered by the pectoral fascia and, forming a vault, the surgical flap consisting of subcutaneous fat and dermis (subcutaneous flap).

The integrity of these elements and retention of vascularisation in the subcutaneous flap are entrusted with the successful incorporation of the biological matrix and, ultimately, the success of the prepectoral implant.

As the biological matrix consists of mammalian collagen (highly conserved structural protein), once implanted inside the human body in of observance of several technical rules, it transforms into tissue through self-assembly. Regenerative medicine sets out the rules for the incorporation of a biological matrix, meaning intimate contact with the vascularised tissue and primary stability.

Mastectomy involves the removal of the entire gland by means of surgical instruments such as electrosurgical cutting, cold scalpel, scissors, forceps and retractors. With regard to the cleavage plane, the surgeon detaches the mammary gland from the subcutaneous tissue and the muscular fascia of the pectoralis major. The gland is detached from the muscle with relative ease, as the presence of a plane of dissection allows the gland to be separated from the deep plane while the subcutaneous plane, given the presence of the crests of Duret, requires much greater care so as not to damage the subcutaneous flap. The primary damage to the subcutaneous flap is vascular damage resulting from the tissue being subjected to excessive traction or thermal trauma. This can result in ischemia or tissue necrosis and, therefore, also in a failure to incorporate the biological matrix which, conversely, requires intimate contact with vital and vascularised tissue.

As the perforator have been removed with the resection of the gland, vascularisation of the subcutaneous flap is entrusted to the peripheral bloodstream, namely the ones located in the subcutaneous tissues of the breast, within the dermis.

With respect to the oncological radicality, the senologist will perform the mastectomy while doing their best to maintain the integrity of the subcutaneous flap, which may also be very thin and, as a result, more sensitive to the traumas associated with the surgical instruments, to the point where sufficient blood supply to promote the incorporation of the matrix is not ensured.

Ultimately, the new suprapectoral (or subcutaneous) plane must be subject to a "friendly" approach from the surgical point of view in order not to damage the vascular structures and the cell population present in the subcutaneous flap. For this reason, the surgeon will prefer to perform the mastectomy with a cold scalpel, and not by electrosurgical cutting as the temperature may harm the life of the cells, just as they will not use cytotoxic substances to irrigate the interior of the breast pocket. The measures required by the new prepectoral technique will be aimed at not causing trauma to the subcutaneous flap in order to promote cellular integrity, a necessary condition for incorporation of the biological matrix. Among the many surgical instruments available to the breast surgeon are retractors, indispensable tools for skin flap elevation and gaining access to the breast pocket.

Prior art tools generally consist of a handle member and at least one longitudinal element called a lever or blade.

State of the art retractors are also known which have multiple blades; for example the retractor described in U.S. patent application 7,384,392 has a handle member and three blades positioned perpendicularly to the plane of the handle member itself.

Regardless of the number of blades with which the retractor is equipped, the distal part of each blade is suitable for gripping and lifting: it may have a blunt or in the form of a hook; in some cases, the distal part of the lever or blade has teeth. It is known that the lever or blade is positioned inside the breast pocket, resting against the subcutaneous flap and pulled upwards by the surgical in order to expose the interior of the breast to the surgeon.

As the cutaneous mantle of the breast consists of soft tissue, the metal lever, or blade, performs its function with understandable ease.

It is known that the lever, or blade, of traditional retractors consists of a rectilinear element which interfaces with soft skin that, in contrast, has a curved surface due to the anatomical concavity.

During the action of lifting, the force applied by the operator is unloaded onto the end of the rectilinear blade which is gripping the subcutaneous flap, generating vascular trauma or injury which is visible, both macroscopically and by fluorescence imaging using a contrast medium such as indocyanine green.

This vascular trauma, in the case of prepectoral (or subcutaneous) implantation of a biological matrix, may be the cause of non-integration of the matrix itself, wound dehiscence due to a lack of blood supply, or necrosis as a result of cell death at the site of the traumatised tissues.

Therefore, the use of a traditional retractor, despite having the positive effect of exposing the inside of the breast pocket, leads to the significant disadvantage of causing trauma to the subcutaneous flap.

The aim of the invention subject of this patent application is the embodiment of a surgical retractor which entails the effective exposure and visibility of the breast pocket and, at the same time, does not compromise the integrity of the subcutaneous flap, resulting in a positive outcome of the breast reconstruction procedure performed generally, though not exclusively, with the use of a prepectoral (or subcutaneous) acellular biological matrix.

Further characteristics and advantages of the invention will become more apparent from the detailed description of a specific but not exclusive embodiment, as illustrated in the accompanying drawings, by way of example and not exhaustive, wherein:

Table 1

FIG. 1: shows a view of the device subject of this present patent application

Table 2

Figure 2:
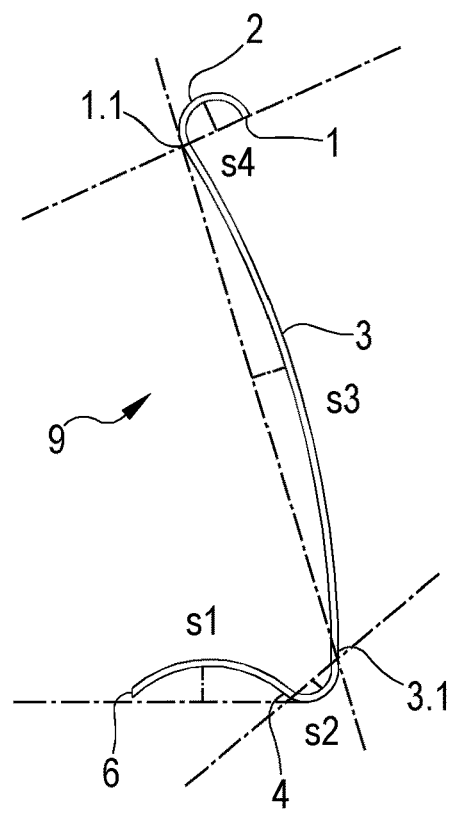
Figure 3:
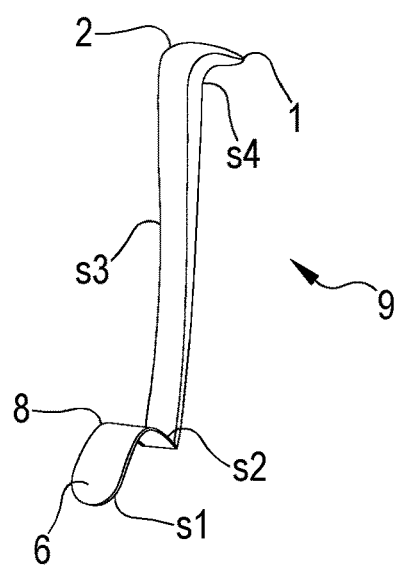

FIG. 2: provides a view of the invention in a preferred initial embodiment;

FIG. 3 provides a side view of the invention in a preferred initial embodiment

Table 3

Figure 4:
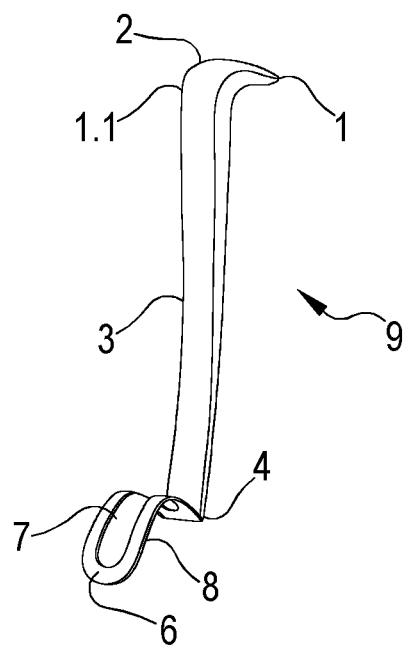
Figure 5:
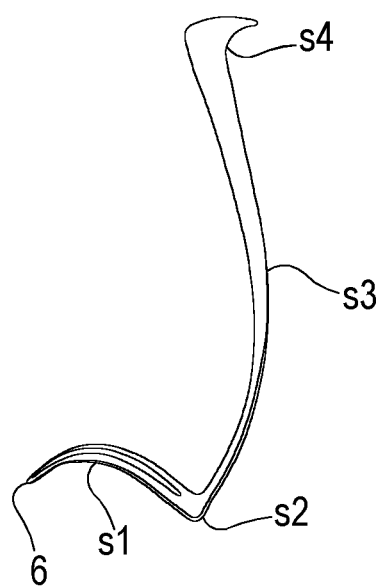

FIG. 4: provides a front view of the invention in a preferred second embodiment;

FIG. 5: provides a side view of the invention in a preferred second embodiment;

Table 4

Figure 6:
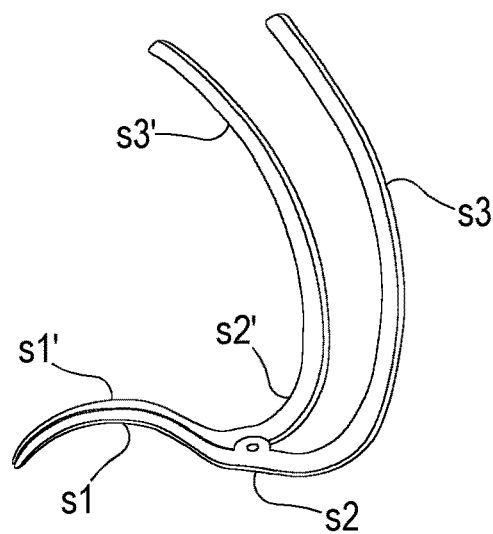
Figure 7:
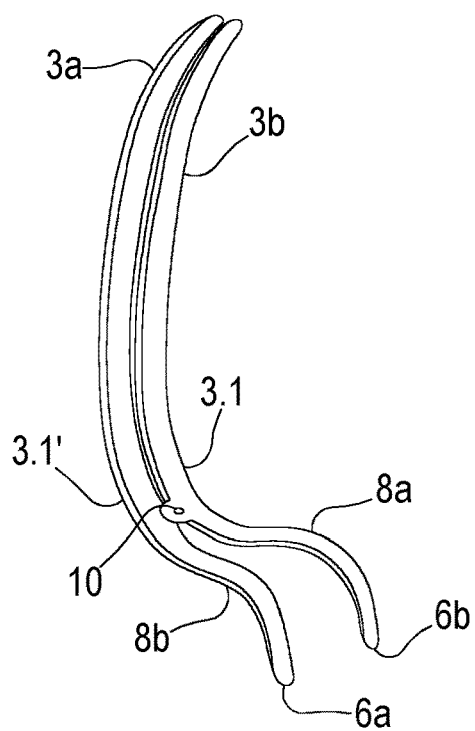

FIG. 6: provides a side view of the invention in the closed position, in a preferred third embodiment;

FIG. 7: provides a side view of the invention in the open position, in a preferred third embodiment;

Table 5

Figure 8:
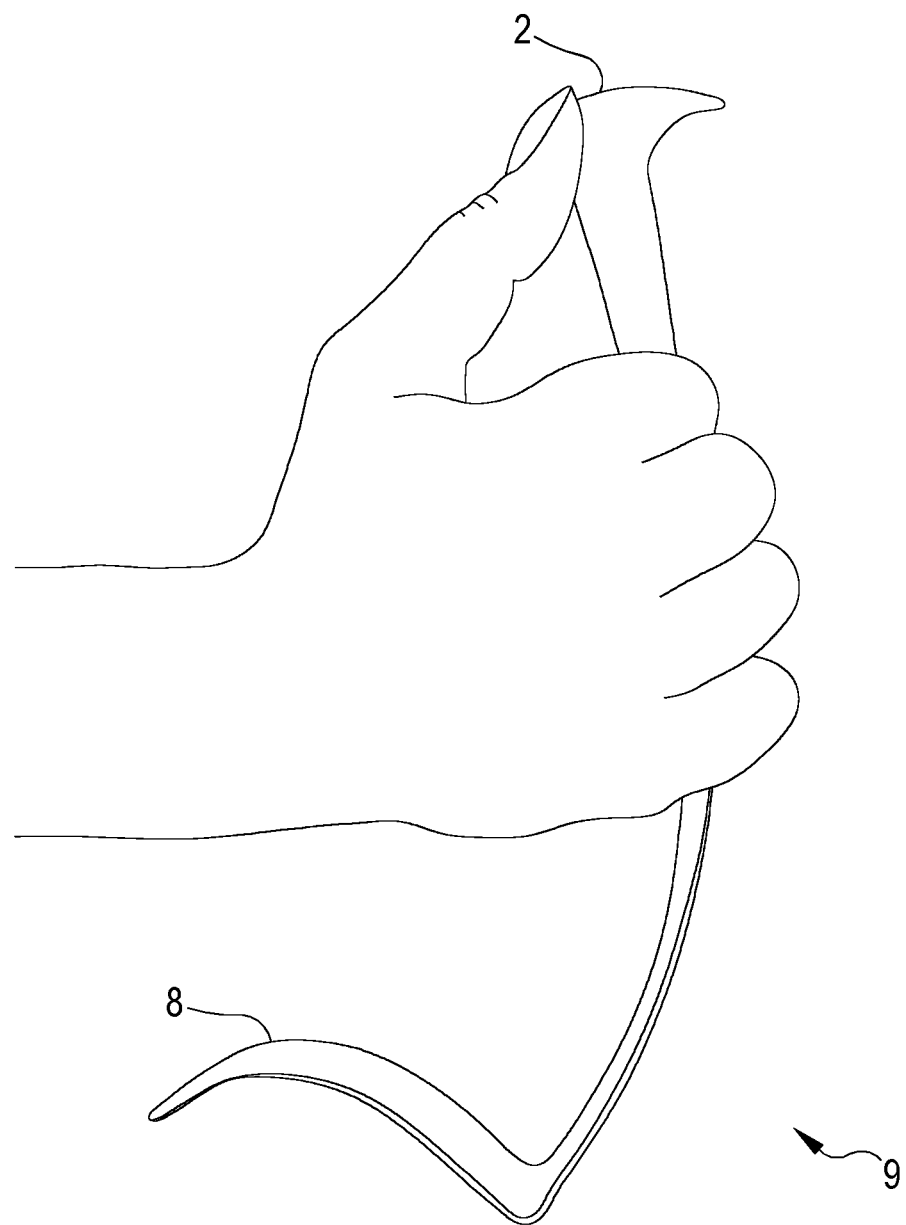

FIG. 8 shows the invention in a preferred initial embodiment during use by the operator.

Table 6

Figure 9:
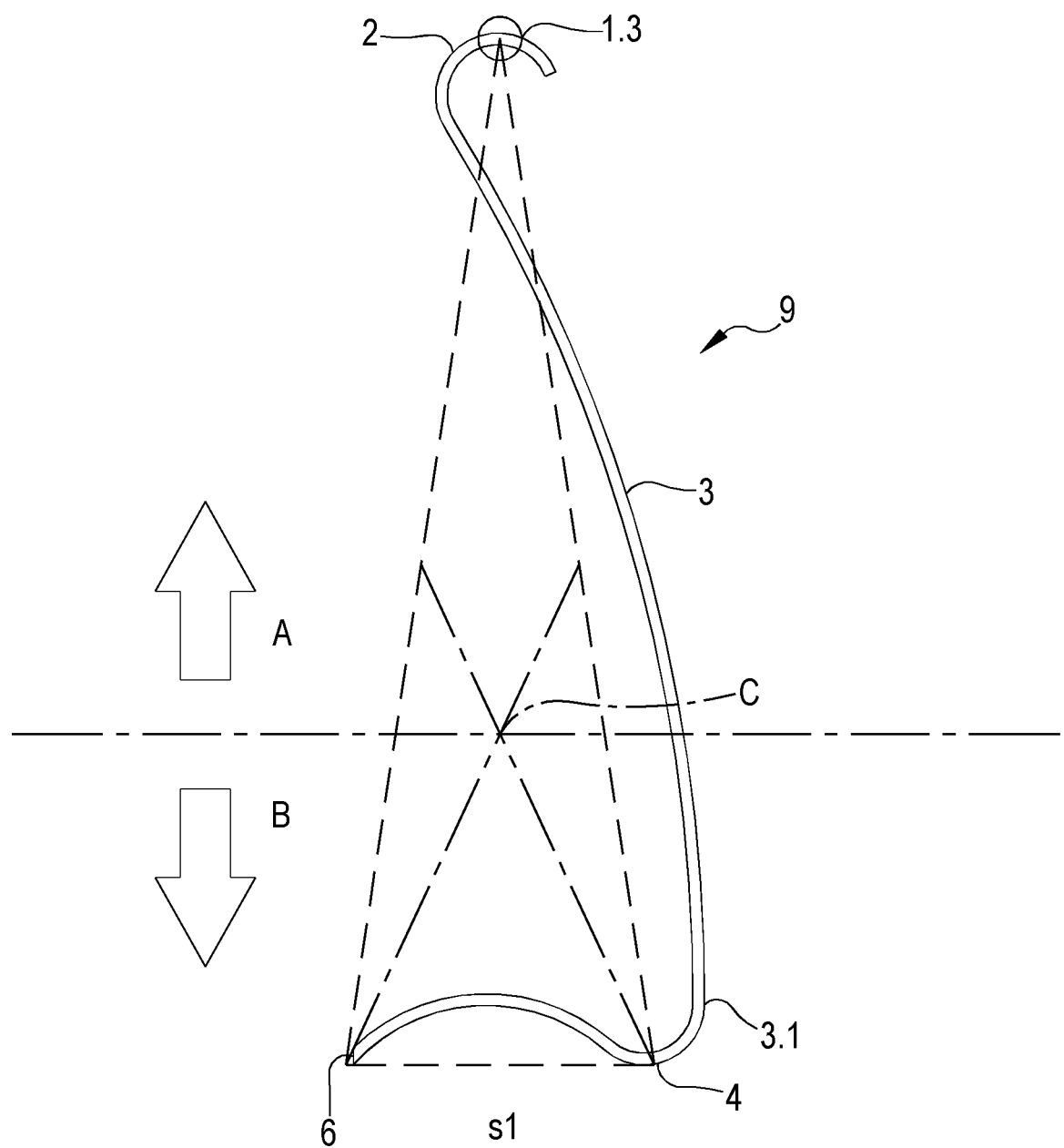

FIG. 9 shows a representation of the extraction force and resistance.

As illustrated by the appended FIGS. 1, 2, 3, 4, 5, 6, 7, 8 and 9), the invention subject of the present patent application consists of a retractor type device (9) equipped with at least one handle member (3) and at least one blade (8).

More specifically, the handle member (3), of which there is at least one, develops longitudinally between an upper end (1.1) and a lower end (3.1), and the blade (8) is between a free end (6) and an opposite end (4).

As evident from the appended FIGS. 1, 2, 3, 4, 5, 6, 7, 8 and 9), and regardless of the preferred but not exclusive embodiments described below, the retractor device (9) in this patent application is formed by a continuous surface, this continuous surface being formed by at least three distinct sections (s1, s2, s3) associated seamlessly with one another.

More specifically, the first section (s1) consists of at least one blade (8) which is convex in shape between the two ends (6.4) of the blade (8); the second section (s2) is positioned between the blade (8); the second section (s2) is positioned between at least one blade (8) and at least one handle member (3) and is concave in shape between the end (4) of at least one blade (8) and the lower end (3.1) of the, at least one, handle member (3).

The third section (s3) consists of the handle member (3) and is concave in shape between a lower end (3.1) an upper end (1.1) of the, at least one, handle member (3).

In a preferred, but not exclusive, initial embodiment (Table 2—FIG. 2 and FIG. 3), the invention subject of this patent application consists of a retractor type device (9) equipped with at least one handle member (3) and at least one blade (8).

More specifically, the handle member (3) develops longitudinally between an upper end (1.1) and a lower end (3.1), and the blade (8) is between a free end (6) and an opposite end (4).

As is evident from FIGS. 2 and 3, the retractor device (9), subject of this patent application, is formed by a continuous surface, this continuous surface being formed by at least four distinct sections (s1, s2, s3, s4) associated seamlessly with one another.

More specifically, the first section (s1) consists of the branch (8) which is convex in shape between the two ends (6.4) of the blade (8); the second section (s2) is positioned between the blade (8) and the handle member (3) and presents as a concave shape between the end (4) of the blade (8) and the lower end (3.1) of the handle member (3).

The third section (s3) consists of the handle member (3) and is concave in shape between a lower end (3.1) an upper end (1.1) of the, at least one, handle member (3).

The fourth section (s4) consists of a convex shape (2) between the upper end (1.1) of the handle member (3) and a free end (1). In a preferred, but not exclusive, embodiment, the free end (1) is chamfered.

In a preferred, but not exclusive, second embodiment (Table 3—FIG. 4 and FIG. 5), the invention subject of this patent application consists of a retractor type device (9) equipped with at least one handle member (3) and at least one blade (8).

More specifically, the handle member (3) develops longitudinally between an upper end (1.1) and a lower end (3.1), and the blade (8) is between a free end (6) and an opposite end (4).

As is evident from FIGS. 2, 4 and 5, the retractor device (9), subject of this patent application, is formed by a single continuous surface, this single continuous surface being formed by at least four distinct sections (s1, s2, s3, s4) associated seamlessly with one another.

More specifically, the first section (s1) consists of the branch (8) which is convex in shape between the two ends (6.4) of the blade (8); the second section (s2) is positioned between the blade (8) and the handle member (3) and presents as a concave shape between the end (4) of the blade (8) and the lower end (3.1) of the handle member (3).

The third section (s3) consists of the handle member (3) and is concave in shape between a lower end (3.1) an upper end (1.1) of the, at least one, handle member (3).

The fourth section (s4) consists of a convex shape (2) between the upper end (1.1) of the handle member (3) and a free end (1). In a preferred, but not exclusive, embodiment, the free end (1) is chamfered.

As is evident in FIGS. 4 and 5, the blade (8) has a cut-out (7) which develops longitudinally between the free end (6) and the end opposite (4).

In a preferred, but not exclusive, third embodiment (Table 4—FIG. 6 and FIG. 7), the invention subject of this patent application consists of a retractor type device (9) equipped with a pair of handle member (3a, 3b) and pair of blades (8a, 8b).

As is evident from FIGS. 1, 6 and 7, the retractor device (9), subject of this patent application, is formed by a pair of continuous surfaces, each of which is formed by at least three distinct sections (s1, s2, s3, and s1', s2', s3').

Specifically, each first section (s1, s1') is seamlessly associated with each second section (s2, s2') and each second section (s2, s2') is seamlessly associated with each third section (s3, s3').

More specifically, each first section (s1, s1') consists of one blade (8a,8b) which is convex in shape between the two ends (6a, 4a) of the blade (8a, 8b); each second section (s2, s2') is positioned between each blade (8a, 8b) and each handle member (3a, 3b) which is concave in shape between the end (4a, 4b) of each blade (8a, 8b) and the lower end (3.1, 3.1') of each handle member (3a, 3b). Each third section (s3, s3') consists of the handle member (3a, 3b) and is concave in shape between a lower end (3.1, 3.1') and upper end (1.1, 1.1') of each handle member (3a, 3b).

With reference to FIGS. 6 and 7, the pair of blades (8a, 8b) is mutually associated by means of a coupling element (10), preferably but not exclusively a through screw, to allow the blades to close or open (8a, 8b) due to the corresponding handle members (3a, 3b) opening or closing (3a, 3b).

With reference to the embodiment shown in FIGS. 6 and 7, when the handle members (3a, 3b) are in the open position, the corresponding blades (8a, 8b) come close and, vice versa, with the handle members (3a, 3b) in the closed position the corresponding blades (8a, 8b) open.

Regardless of the preferential embodiments described herein, and without modifying the essential characteristic aspects, the curvature of at least one blade (8) may be the result of several radii of curvature supporting the curvature of the interior chamber of the breast pocket.

Furthermore, regardless of the preferred embodiments described herein, and without modifying the essential characteristic aspects, the embodiment of the retractor device (9), as described, can be equipped with a generic external light source to illuminate the surgical site.

Regardless of the preferred embodiments described herein, and without modifying the essential characteristic aspects, the embodiment of the retractor device (9), as previously described, allows the effective exposure and visibility of the breast pocket and, at the same time, does not compromise the integrity of the subcutaneous flap, resulting in a positive outcome of the breast reconstruction procedure performed generally, though not exclusively, with the use of a prepectoral (or sub-cutaneous) acellular biological matrix. With reference to FIG. 8, the hand of the surgeon holds the retractor device (9) by means of the concave handle (3) allowing an ergonomic position to be maintained and a lifting action by means of the convex blade (8).

According to the invention, subject of this patent application, the stress from the external traction applied to the subcutaneous flap to lift the skin will be spread over a larger support surface thereby reducing tissue damage compared to that resulting from the action of a lever or rectilinear blade, damage which is further increase if the skin is hooked.

More specifically, the angle of the handle member exerts significant leverage on the surgical site, ensuring less energy dissipation than that produced by a retractor with a handle member positioned perpendicularly to the blade.

As shown in FIG. 9, the secant of the arch which constitutes the section (s1) between the free end (6) and end (4) of the blade (8), defines the base of an acute triangle whose sides are defined by the two segments comprised, respectively, between the free end (6) and the centre of curvature (1.3) of the upper free end (2), and between the end (4) of the blade (8) and the centre of curvature of the upper free end (2).

The force applied to lift the skin (traction vector A) and the resistance of the skin itself (coupling-resistance vector B) coincide, passing through the centre of gravity (C) of the defined actuate triangle as described above.

It follows that the angle of the handle member (3) allows the hand of the surgical assistant to have the most ergonomic position in relation to the lifting action of the handle member itself, and that the triple-curved shape of the retractor device (9) in the embodiment described, for concentrated load in the surgical site, only requires the slight inclination of the wrist to perform the act of exposing the breast pocket, decreasing the traction force required for lifting.

The invention claimed is:

1. A retractor device (9) for breast reconstruction surgery, comprising:
   at least one handle (3) with longitudinal development between an upper end (1.1) and a lower end (3.1) and at least one offshoot (8), the at least one offshoot (8) having a free end (6) and an opposite end (4);
   wherein the at least one offshoot (8) is configured to be placed inside a breast pocket and to lift the skin to expose the interior of the breast;
   wherein the retractor device (9) is formed as a continuous structure extending from the upper end (1.1) to the free end (6),
   wherein the continuous structure includes a first continuous surface and a second continuous surface that faces an opposite direction relative to the first continuous surface, said first continuous surface being formed by at least three distinct sections (s1, s2, s3) joined seamlessly, wherein the at least three distinct sections (s1, s2, s3) comprise a first section (s1), a second section (s2), and a third section (s3);
   wherein the first section (s1) of the first continuous surface consists of the at least one offshoot (8) and takes the form of a convex figure from the free end (6) to the opposite end (4) of the at least one offshoot (8);
   wherein the second section (s2) of the continuous surface is positioned between the at least one offshoot (8) and the at least one handle (3) and takes the form of a concave figure between the opposite end (4) of the at least one offshoot (8) and the lower end (3.1) of the at least one handle (3); and
   wherein the third section (s3) of the first continuous surface consists of the at least one handle (3) and takes the form of a concave figure between the lower end (3.1) and the upper end (1.1) of the at least one handle (3).

2. The device as in claim 1, wherein the at least three distinct sections (s1, s2, s3) include a fourth section (s4) consisting of a convex FIG. (2) between the upper end (1.1) of the at least one handle (3) and a free end (1) of the fourth section (s4).

3. The device as in claim 2, wherein the free end (1) of the fourth section (s4) is blunt.

4. The device as in claim 1, wherein the at least one offshoot (8) has a through opening (7) that extends longitudinally between the free end (6) and the opposite end (4).

5. A retractor device (9) for breast reconstruction surgery comprising:
   at least one handle (3) with longitudinal development between an upper end (1.1) and a lower end (3.1), and at least one offshoot (8), the at least one offshoot (8) having a free end (6) and an opposite end (4),
   wherein the at least one offshoot (8) is configured to be placed inside a breast pocket and to lift the skin to expose the interior of the breast;

wherein said retractor device (9) is formed as a pair of continuous surfaces, each of said continuous surfaces extending from the upper end (1.1) to the free end (6);

wherein each of the continuous surfaces includes a first continuous surface and a second continuous surface that faces an opposite direction relative to the first continuous surface, said first continuous surface being formed by at least three distinct sections (s1, s2, s3, s1', s2', s3') joined seamlessly, wherein each of the at least three distinct sections (s1, s2, s3, s1', s2', s3') comprise a first section (s1, s1'), a second section (s2, s2') and a third section (s3, s3');

wherein each first section (s1, s1') of the first continuous surface consists of one offshoot (8a, 8b) of said at least one offshoot and takes the form of a convex figure from the free end (6) to the opposite end (4) of the at least one offshoot (8), wherein each third section (s3, s3') of the continuous surface consists of one handle (3a, 3b) of said at least one handle, wherein each second section (s2, s2') of the first continuous surface is positioned between each offshoot (8a, 8b) and each handle (3a, 3b); and wherein the pair of continuous surfaces is joined together by means of a joint element (10) configured for allowing the offshoots (8a, 8b) to close and open due to the corresponding handles (3a, 3b) opening and closing respectively.

6. A retractor device (9) for breast reconstruction surgery comprising
at least one handle (3) with longitudinal development between an upper end (1.1) and a lower end (3.1); and
at least one offshoot (8), the at least one offshoot (8) having a free end (6) and an opposite end (4),
wherein the at least one offshoot (8) is configured to be placed inside a breast pocket and to lift the skin to expose the interior of the breast;

wherein said retractor device (9) is formed as a continuous surface, said continuous surface being formed by at least three distinct sections (s1, s2, s3) joined seamlessly, wherein the at least three distinct sections (s1, s2, s3) comprise a first section (s1), a second section (s2) and a third section (s3);

wherein the first section (s1) consists of the at least one offshoot (8) and takes the form of a convex figure between the free end (6) and the opposite end (4) of the at least one offshoot (8);

wherein the second section (s2) is positioned between the at least one offshoot (8) and the at least one handle (3) and takes the form of a concave figure between the opposite end (4) of the at least one offshoot (8) and the lower end (3.1) of the at least one handle (3);

wherein the third section (s3) consists of the at least one handle (3) and takes the form of a concave figure between the lower end (3.1) and the upper end (1.1) of the at least one handle (3);

wherein the at least three distinct sections (s1, s2, s3) include a fourth section (s4) consisting of a convex FIG. 2) between the upper end (1.1) of the at least one handle (3) and a free end (1) of the fourth section (s4); and wherein the free end (6) and the opposite end (4) of the first section (s1) define a base of an acute triangle whose sides are defined by two segments comprised respectively between the free end (6) of the at least one offshoot (8) and a centre of curvature (1.3) of the convex FIG. (2) of the fourth section (s4) and between the opposite end (4) of the at least one offshoot (8) and said centre of curvature (1.3).

* * * * *